United States Patent
Gulyas et al.

(10) Patent No.: US 8,633,327 B2
(45) Date of Patent: Jan. 21, 2014

(54) PROCESS FOR PREPARING DIVINYLARENE DIOXIDES

(75) Inventors: Gyongyi Gulyas, Lake Jackson, TX (US); Robert J. Wright, Houston, TX (US); Martha P. Hernandez, Richwood, TX (US); Eric P. Ripplinger, Lake Jackson, TX (US)

(73) Assignee: Dow Global Technologies Inc., Midland, MI (US)

(*) Notice: Subject to any disclaimer, the term of this patent is extended or adjusted under 35 U.S.C. 154(b) by 0 days.

(21) Appl. No.: 13/583,035

(22) PCT Filed: Mar. 23, 2011

(86) PCT No.: PCT/US2011/029494
§ 371 (c)(1),
(2), (4) Date: Sep. 6, 2012

(87) PCT Pub. No.: WO2011/119655
PCT Pub. Date: Sep. 29, 2011

(65) Prior Publication Data
US 2013/0006000 A1    Jan. 3, 2013

(51) Int. Cl.
*C07D 301/16* (2006.01)
(52) U.S. Cl.
USPC .................................................. 549/526

(58) Field of Classification Search
USPC ........................................................ 549/526
See application file for complete search history.

(56) References Cited

U.S. PATENT DOCUMENTS

| 2,977,374 A | 3/1961 | Phillips et al. |
| 2,982,752 A | 5/1961 | Phillips et al. |
| 3,567,396 A | 3/1971 | Setzler, Jr. |

FOREIGN PATENT DOCUMENTS

| JP | 09-286750 | * 11/1997 |
| JP | 09286750 | 11/1997 |
| WO | 2009119513 | 10/2009 |
| WO | 2011056381 | 5/2011 |
| WO | 2011084687 | 7/2011 |

OTHER PUBLICATIONS

Organic synthesis coll., vol. 5. 904, 1973.

* cited by examiner

*Primary Examiner* — Taylor Victor Oh

(57) ABSTRACT

A process for preparing a divinylarene dioxide including reacting (a) at least one divinylarene; and (b) at least one peracid oxidant compound, under conditions to form a divinylarene dioxide product; wherein the peracid oxidant compound is capable of providing an increased yield of a divinylarene dioxide product.

22 Claims, No Drawings

PROCESS FOR PREPARING DIVINYLARENE DIOXIDES

BACKGROUND OF THE INVENTION

1. Field of the Invention

The present invention is related to a process for preparing divinylarene dioxides, particularly divinylarene dioxides derived from divinylbenzene. More specifically, the present invention relates to a process for preparing a divinylarene dioxide by epoxidizing a divinylarene with at least one peracid oxidant compound capable of providing an increased yield of a divinylarene dioxide product.

Divinylarene dioxides, particularly divinylbenzene dioxide (DVBDO) and others which are derived from divinylbenzene (DVB) are a class of diepoxides which can be used as either a reactive diluent or as the main epoxy resin matrix in an epoxy thermoset formulation. DVBDO itself has a very low liquid viscosity (for example less than about 20 centipoises (0.02 Pas) making DVBDO especially useful in the preparation of low viscosity epoxy formulations. The epoxy formulations made from DVBDO are useful as intermediates in the production of various other products. For example, epoxy formulations made from DVBDO are suitable for use in the fields of coatings, composites, and molding compositions.

2. Description of Background and Related Art

Epoxidation of divinylarene, such as DVB, presents several challenges in an industrial process for making divinylarene dioxide, such as DVBDO, because the divinylarene contains two terminal olefin groups in the molecule as compared with mono-olefins. If some of the olefin groups of a diolefin compound are not converted to epoxides (for example as shown in the simplified Reaction Scheme I below with m-DVB) a monoxide such as divinylbenzene monoxide (DVBMO) would remain in the resultant crude product.

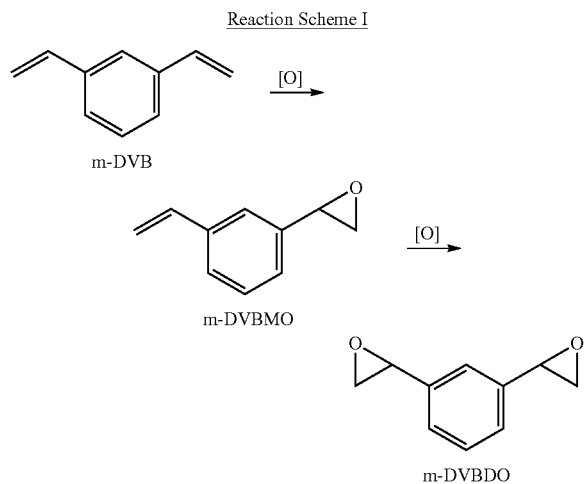

The boiling points of the undesired monoxide such as DVBMO and the desired dioxide product such as DVBDO are so close to each other that a highly efficient separation method would be required to remove the undesired DVBMO from the desired product DVBDO, thus increasing the cost and complexity of the process for producing DVBDO. DVB and DVBMO are also prone to polymerization which adds to the complexity of the process.

Heretofore, the epoxidation of DVB using peracetic acid has been disclosed in the art. However, the yields of DVBDO have been very low (less than 50%). For example, Japanese Patent No. 09286750 discloses a process for producing p-DVBDO using peracetic acid in anhydrous ethyl acetate at 30° C. in 30% yield. The DVBDO product is isolated by distillation.

U.S. Pat. No. 2,977,374 ("the '374 patent") discloses epoxidizing DVB using peracetic acid in anhydrous ethyl acetate at 70° C. in a continuous reactor followed by isolating the product by distillation. The '374 patent reports a DVBDO yield of 49%. In the '374 patent, an 81% yield of styrene oxide is reported in a similar process. Although styrene and DVB are structurally similar, epoxidation of the two double bonds in the same molecule will not necessarily provide comparable results, as shown in the '374 patent. Epoxidation using peracetic acid generates acetic acid as a co-product and acetic acid is known to readily react with the resulting vinyl-epoxide type product to produce a hydroxy ester byproduct, thereby lowering the yield of the epoxide product. Furthermore, vinyl-epoxides are also prone to rearrangement reactions when subjected to acids. In the case of a diolefin the same molecule has to take part in the reaction twice. Consequently, the residence time of the epoxide product in the reaction mixture is longer and the epoxide product has a greater probability to undergo side reactions.

SUMMARY OF THE INVENTION

One embodiment of the present invention is directed to a process for preparing a divinylarene dioxide including reacting (a) at least one divinylarene; (b) at least one oxidant; wherein the oxidant comprises a peracid compound capable of providing a divinylarene dioxide product yield of greater than 50; (c) an optional solvent; and (d) an optional basic compound; wherein the reaction is carried out under homogeneous reaction conditions sufficient to form a divinylarene dioxide product.

Another embodiment of the present invention is directed to a process for preparing a divinylarene dioxide comprising reacting (a) at least one divinylarene; (b) at least one oxidant; wherein the oxidant comprises an aromatic peracid compound; (c) an optional solvent; and (d) an optional organic base miscible with the divinylarene; wherein the reaction is carried out under homogeneous reaction conditions sufficient to form a divinylarene dioxide product.

Yet another embodiment of the present invention is directed to a process for preparing a divinylarene dioxide comprising reacting (a) at least one divinylarene; (b) at least one oxidant, wherein the oxidant comprises a peracid compound; (c) at least one basic compound; and (d) an optional solvent; wherein the reaction is carried out under heterogeneous conditions sufficient to form a divinylarene dioxide product.

Some of the advantages of the process of the present invention include for example: (1) the process provides a high conversion of a divinylarene, such as DVB, to a divinylarene dioxide, such as DVBDO; and a high selectivity (above 50%) for epoxide formation; (2) the use of heterogeneous systems suppresses by-product formation due to the opening of the epoxide ring or its rearrangement that can be caused by subjecting the epoxide to acidic environment; the by-product formation is suppressed because the acid formed is extracted into either an aqueous buffer solution as a salt or precipitates out from the organic reaction mixture as a salt; (3) the use of homogenous conditions excludes water which diminishes side reactions caused by acidic components; (4) the use of an optional organic base in homogeneous systems may form a salt with the acid, hence preventing the acid from reacting with the epoxide; and (5) the use of aromatic peracids such as m-chloroperbenzoic or perbenzoic acid provide for a much faster reaction than an aliphatic peracetic acid, which also limits the time until the divinylarene dioxide product, for example DVBDO, is subjected to the presence of acids.

DETAILED DESCRIPTION OF THE INVENTION

In its broadest scope, the present invention includes a process for preparing a divinylarene dioxide by reacting (a) at least one divinylarene with (b) at least one peracid compound as the oxidant. In one embodiment of the present invention the peracid compound and divinylarene reacts in a homogeneous medium, and is capable of providing a divinylarene dioxide product yield of greater than 50 percent. In another embodiment, the divinylarene dioxide is prepared in a heterogeneous system. In one embodiment of the heterogeneous reaction, the epoxidation is carried out in an organic-aqueous buffered system and in another embodiment in a solid liquid system. And, in still another embodiment, the divinylarene dioxide product such as DVBDO is prepared by epoxidizing a divinylarene such as DVB with an aromatic peracid compound instead of an aliphatic peracid compound in a homogeneous system.

In other embodiments, the process of the present invention may be carried out in the presence of other components such as at least one solvent and/or at least one basic compound or pH control agent in sufficient quantities and under conditions to form a divinylarene dioxide product. Optionally, the reaction process may be carried out further including other additives such as a catalyst and/or a phase transfer salt.

The process of the present invention advantageously provides a high yield (for example yields of greater than 50%) process for the synthesis of a divinylarene dioxide such as DVBDO. Other improvements of the present invention process over known procedures include for example the use of heterogeneous reaction conditions to remove the carboxylic acid co-product generated from the oxidant, minimizing the exposure of the divinylarene product to acidic environment that can lead to unwanted side reactions.

Generally, in the process of the present invention, a divinylarene, and/or optionally any other desirable additives such as a basic compound or a solvent are contacted with a peracid oxidizing agent in a reactor, which may be batch or continuous; and the reactants are allowed to react to produce the corresponding divinylarene dioxide. Any co-produced salts, the solvent, and the optionally-present additives may be removed from the divinylarene dioxide product present in the reaction mixture to give a usable divinylarene dioxide product. In turn, the divinylarene dioxide product may optionally be purified further, for example, by distillation, crystallization, and other purification methods known in the art.

As an illustration of one embodiment of the present invention, for example, a divinylarene dioxide such as DVBDO may be prepared by dissolving a divinylarene such as DVB in a solvent such as dichloromethane and then using an oxidant such as perbenzoic acid as the oxidizing agent to epoxidize the DVB to form DVBDO. The epoxidation reaction may be carried out at a temperature of between about −20° C. to about 100° C. After the epoxidation is completed, the solvent, the co-produced acid originating from the oxidant and other additives such as optional organic base (for example pyrazole) may be removed from the product; and if desired, the product may be purified by known means such as distillation.

The source of divinylarene useful in the present invention may come from any known sources and particular to known processes for preparing divinylarenes. For example, divinylarenes can be prepared with salt or metal wastes from arenes and ethylene.

In one embodiment of the present invention, the divinylarene useful in the present invention may comprise any substituted or unsubstituted arene nucleus bearing two vinyl groups in any ring position. The arene may include for example benzene, substituted benzenes, or (substituted) ring-annulated benzenes, and mixtures thereof. In one embodiment, divinylbenzene may be ortho, meta, or para isomers or any mixture thereof. Additional substituents may consist of oxidation-resistant groups including for example saturated alkyl, aryl, halogen, nitro, isocyanate, or RO— (where R may be saturated alkyl or aryl), or mixtures thereof. Ring-annulated benzenes may include for example naphthlalene, tetrahydronaphthalene, and the like, and mixtures thereof.

In another embodiment, the divinylarene may contain quantities of substituted arenes. The amount and structure of the substituted arenes depend on the process used in the preparation of the divinylarene. For example, DVB prepared by a known dehydrogenation of diethylbenzene (DEB) may contain ethylvinylbenzene (EVB) and DEB.

The divinylarene used in the process of the present invention may include for example divinylbenzene, divinylnaphthalene, divinylbiphenyl, divinyldiphenylether, and mixtures thereof.

The concentration of the divinylarene used in the present invention may range generally from about 1 weight percent (wt %) to about 100 wt %, preferably from about 5 wt % to about 95 wt %, and more preferably from about 20 wt % to about 80 wt %.

The oxidizing agent or oxidant useful in the present invention includes an oxygen transfer type oxidant, such as for example the aliphatic and aromatic compounds under the general classification of peracid compounds. For example, the peracid oxidant useful in the present invention may include performic acid, peracetic acid, m-chloroperbenzoic acid, perbenzoic acid, monoperoxophtalic acid, and mixtures thereof.

In one embodiment, the peracid oxidant preferably comprises at least one aromatic peracid compound; under homogeneous conditions, sufficient to form a divinylarene dioxide product. In another embodiment, the peracid oxidant preferably comprises at least one aromatic peracid compound; under heterogeneous conditions, sufficient to form a divinylarene dioxide product. The aromatic peracid oxidant useful in the above embodiments of the present invention may include, for example, m-chloroperbenzoic acid, perbenzoic acid, monoperoxophtalic acid and mixtures thereof.

The peracids used in the present invention can be used as solids or dissolved in organic solvents or water, dependent on the characteristics of the acids. For example, peracetic acid can be used as an aqueous solution or in an organic solvent such as ethyl acetate. Perbenzoic acid can be delivered to react with the divinyl arene as a solution in an organic solvent such as dichloromethane or as a solid which will dissolve in the divinylarene or in the divinylarene solvent mixture if solvent is used.

The molar excess of the oxidant compared to the divinylarene in the present invention may range from about 1 mol/mol to about 20 mol/mol, preferably from about 2 mol/mol to about 10 mol/mol, and more preferably from about 2 mol/mol to about 4 mol/mol.

The peracids used in the present invention can be isolated or generated in-situ. For example, peracids can be generated from the corresponding acid and hydrogen peroxide or by the reaction of aldehydes and air. The in-situ generation from the acid and hydrogen peroxide generally requires an acid catalyst. Due to the acid sensitivity of DVBDO the applicability of the in-situ procedure may be limited. However, the peracids may be generated and then used after generation without isolation if desired. In the case where strong acid catalysis is used for peracid generation, the strong acid might be neutralized prior to epoxidation.

When the epoxidation of the divinylarene is conducted under heterogeneous conditions, a basic compound is preferably used. The basic compound can be delivered as an aqueous solution resulting in a liquid-liquid, aqueous-organic heterogeneous system or it can also be used as a solid resulting in a liquid-solid system. The basic compound can favorably affect undesired side reactions caused by the acidic co-products forming from the peracid oxidant. For example, basic compounds used in the present invention may include the inorganic bases sodium or potassium carbonate, sodium or potassium hydrogencarbonate, sodium or potassium phosphate, sodium or potassium hydroxide and mixtures thereof.

The molar ratio of the basic compound compared to the peracid can range from about 0.5 to about 5 mol/mol; preferably from about 1 to about 3 mol/mol and most preferably from about 1.1 to about 2 mol/mol.

In the case of an aqueous buffer, the preferred pH range is from about 5 to about 11, preferably from about 6 to about 9, and more preferably from about 7 to about 8.

When the reaction is conducted under homogeneous conditions, the basic compound is an optional component. In this embodiment of the present invention, the divinylarene is epoxidized in the presence or the absence of a solvent and the basic compound is miscible with the divinylarene or the divinylarene and organic solvent solutions. Examples of such basic compounds include aliphatic or aromatic nitrogen bases, for example, triethyl amine, pyrazole, pyridine and the like. The molar ratio of the optional basic compound compared to the peracid can range from about 0.5 mol/mol to about 5 mol/mol; preferably from about 1 mol/mol to about 3 mol/mol and most preferably from about 1.1 mol/mol to about 2 mol/mol.

The solvent useful in the process of the present invention may include for example any inert organic solvent that is inert to the oxidant under the reaction conditions. For example, the solvent may include halogenated alkanes such as dichloromethane; aromatics such as toluene or xylene; polar organic solvents such as dimethyl formamide (DMF); nitriles such as acetonitrile; ethers such as tetrahydrofuran (THF), dioxane or dimethoxyethane; alcohols such as tert-amyl alcohol, tert-butanol, methanol, ethanol, Dowanol PM or isopropanol; fluorinated alcohols such as trifluoroethanol; chlorinated hydrocarbons solvents such as dichloromethane or dichloroethane; esters such as ethylacetate; ketones such as acetone; and mixtures thereof.

In a preferred embodiment, the solvent useful in the present invention may include for example, acetonitrile, methanol, dioxane, dimethoxyethane, THF, dichloromethane, toluene, DMF, ethyl acetate or mixture of two or more solvents The concentration of the solvent used in the present invention may range generally from about 0 wt % to about 99 wt %, preferably from 0.1 wt % to about 91 wt %, more preferably from about 5 wt % to about 95 wt %, and most preferably from about 20 wt % to about 80 wt %.

One of the optional components useful in the heterogeneous embodiment of the present invention may include for example a phase transfer agent. The phase transfer agent may include for example tetraakyl, tetraaryl, or mixed alkyl-aryl ammonium hydroxides or salts; and mixtures thereof. In one embodiment, the phase transfer agent may include for example the following compounds: tertrabutylammonium hydroxide, -chloride or -acetate; tetraphenylammonium hydroxide, -chloride or -acetate; and mixtures thereof.

The molar ratio of the divinylarene and phase transfer agent can range from 0 mol/mol to about 5 mol/mol, preferably from about 0.01 mol/mol to about 5 mol/mol, more preferably from about 0.01 mol/mol to about 2 mol/mol and most preferably from about 0.1 mol/mol to about 0.5 mol/mol.

One of the optional components useful in the present invention may include a catalyst. These catalysts may be soluble in the reaction mixture (homogeneous catalysts) insoluble (heterogeneous catalysts), or homogeneous catalysts supported on a variety of materials.

Examples of heterogeneous catalysts include for example gold nanoparticles. Transition metal complexes can be used as homogeneous catalysts such as various Mn(III) salen complexes such as Jacobsen catalyst; Ru(II)-porphyrin complexes; dioxo-ruthenium(VI)-porphyrin complexes; dioxoosmium(VI)-porphyrin complexes; Mn(II) complexes containing polypyridylic ligands; iron-phenantroline complexes; and mixtures thereof. The homogeneous catalysts can be immobilized using a variety of support materials. For example, the support material may include chitosan membranes; carbon xerogels; silicas such as SBA-15 and MCM 41; aluminas; MgO; clays; activated carbon; polystyrene; and mixtures thereof.

The preparation of divinylarene dioxides without co-production of undesirable by-products may be achieved for example by (i) adding to a reactor the following reactants: a divinylarene and an aqueous solution of a basic compound, the optional additives such as an inert organic solvent; (ii) contacting the reactants with the peracid oxidant; and then (iii) allowing the components in the reaction mixture to react under reaction conditions to produce the corresponding divinylarene dioxide.

The reaction conditions include carrying out the reaction under a temperature, generally in the range of from about $-20°$ C. to about $100°$ C., preferably from about $5°$ C. to about $80°$ C., more preferably from about $10°$ C. to about $70°$ C., and most preferably from about $20°$ C. to about $60°$ C.

The pressure of the reaction may be generally from about 10.13 kPa to about 1013 kPa [0.1 atmosphere (atm) to about 10 atm].

The pH of the reaction may be generally from about 5 to about 11, preferably from about 6 to about 9; and more preferably from about 7 to about 8.

The reaction process of the present invention may be a batch or a continuous process. The reactor used in the process may be any reactor and ancillary equipment well known to those skilled in the art.

During the reaction for the preparation of divinylarene dioxide, an equivalent amount of carboxylic acid co-product forms in the reaction mixture. In the case of buffered systems this carboxylic acid is converted to a salt. The formed co-product can be removed from the reaction mixture by separating the organic phase and the aqueous phase of the reaction mixture followed by an appropriate number of water washes of the organic phase. In the case of using excess of the peracid oxidant compared to the divinyl arene the peracid can be converted into the appropriate carboxylic acid by using a suitable reducing agent such as sodium sulfite. The generated carboxylic acid then can readily be extracted into the aqueous phase by a basic buffer and separated from the divinylarene dioxide product. One advantage of the present invention process is that other undesirable oxidized by-products and derivatives, such as for example carbonyl compounds and hydrolyzed epoxy products, are not formed in any appreciable quantities using the process of the present invention.

After the reaction of the present invention, the undesirable by-products and any remaining reactants and solvent, may be removed to recover a sufficient amount of usable divinylarene dioxide product. Then the product may optionally be purified by well-known means in the art such as by chromatography, distillation, crystallization, and the like.

One advantage of the present invention process is that high yields of divinylarene dioxides may be produced by the process of the present invention. With high yields of divinylarene dioxides produced, the process of the present invention advantageously requires less recycle and produces less waste.

The "high yield" of divinylarene dioxide produced by the process of the present invention is generally greater than about 30%; preferably, greater than about 50%, and more preferably greater than about 70%. In one embodiment, the yield of divinylarene dioxide produced by the process of the present invention ranges from about 50% to about 100%. In another embodiment, the yield may be from about 60% to about 100%; and yet another embodiment the yield from about 70% to about 100% based on divinylarene starting material.

In one embodiment of the process of the present invention, the process for preparing a divinylarene dioxide may generally comprise the steps of:

(a) contacting at least one divinylarene with a peracid oxidant compound; optionally with at least one solvent; to produce a divinylarene dioxide product in a reaction mixture;

(b) separating the divinylarene dioxide product formed in step (a) from the reaction mixture of step (a); and (c) optionally, recovering and/or recycling the solvent and catalyst from the reaction mixture of step (a)

In other embodiments of the process of the present invention, the process for preparing a divinylarene dioxide may include one or more the following optional steps: (i) reacting a peracid compound with DVB in a pH controlled organic-aqueous buffered heterogeneous reaction; (ii) reacting a peracid compound with DVB in the presence of an organic base in a homogeneous reaction; (iii) reacting a peracid compound with DVB in the presence of an inorganic base in a heterogeneous solid-liquid phase reaction; (iv) separating an acid/salt co-product from DVBDO product by phase separation; (v) decomposing an excess peracid compound with a reducing agent such as $Na_2SO_3$; (vi) separating an organic phase containing the DVBDO product from an aqueous phase containing a salt co-product; (vii) solvent is removed from DVBDO; or (viii) distilling DVBDO to give a high purity DVBDO product.

The divinylarene dioxides prepared by the process of the present invention, particularly those derived from divinylbenzene such as for example divinylbenzene dioxide (DVBDO), are class of diepoxides having a relatively low liquid viscosity but a higher rigidity than conventional epoxy resins.

The divinylarene dioxide useful in the present invention may comprise, for example, any substituted or unsubstituted arene nucleus bearing two vinyl groups in any ring position. The arene portion of the divinylarene dioxide may comprise benzene, substituted benzenes, ring-annulated benzenes, substituted ring-annulated benzenes, homologously bonded benzenes, substituted homologously bonded benzenes, or mixtures thereof. The divinylarene portion of the divinylarene dioxide may be ortho, meta, or para isomers or any mixture thereof. Additional substituents may consist of $H_2O_2$-resistant groups including saturated alkyl, aryl, halogen, nitro, isocyanate, or RO— (where R may be a saturated alkyl or aryl). Ring-annulated benzenes may comprise for example naphthalene, tetrahydronaphthalene, and the like. Homologously bonded (substituted) benzenes may comprise for example biphenyl, diphenylether, and the like.

The divinylarene oxide product prepared by the process of the present invention may be illustrated generally by general chemical Structures I-IV as follows:

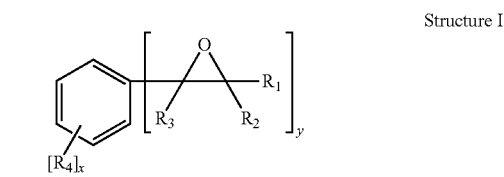

Structure I

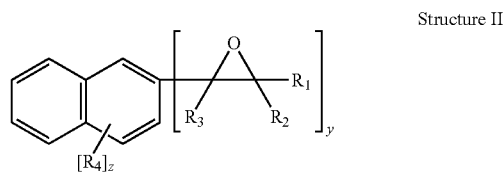

Structure II

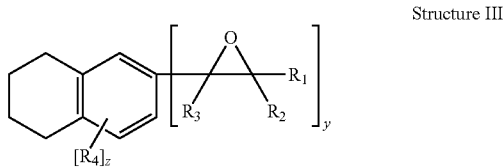

Structure III

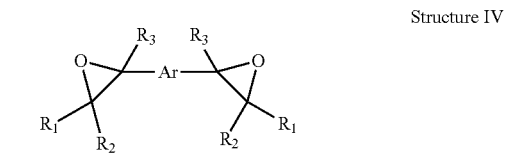

Structure IV

In the above Structures I, II, III and IV of the divinylarene dioxide product of the present invention, each $R_1$, $R_2$, $R_3$ and $R_4$ individually may be hydrogen, an alkyl, cycloalkyl, an aryl or an aralkyl group; or a oxidant-resistant group including for example a halogen, a nitro, an isocyanate, or an RO group, wherein R may be an alkyl, aryl or aralkyl; x may be an integer of 0 to 4; y may be an integer greater than or equal to 2; x+y may be an integer less than or equal to 6; z may be an integer of 0 to 6; and z+y may be an integer less than or equal to 8; and Ar is an arene fragment including for example, 1,3-phenylene group.

The divinylarene dioxide product produced by the process of the present invention may include for example alkyl-vinyl-arene monoxides depending on the presence of alkylvinylarene in the starting material.

In one embodiment of the present invention, the divinylarene dioxide produced by the process of the present invention may include for example divinylbenzene dioxide, divinylnaphthalene dioxide, divinylbiphenyl dioxide, divinyldiphenylether dioxide, and mixtures thereof.

Structure V below illustrates an embodiment of a preferred chemical structure of a DVBDO useful in the present invention:

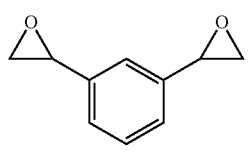

Structure V

Structure VI below illustrates another embodiment of a preferred chemical structure of the DVBDO useful in the present invention:

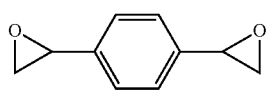

Structure VI

When DVBDO is prepared by the process of the present invention, it is possible to obtain one of three possible isomers: ortho, meta, and para. Accordingly, the present invention includes a DVBDO illustrated by any one of the above Structures individually or as a mixture thereof. Structures V and VI above show the meta (1,3-DVBDO) and para isomers of DVBDO, respectively. The ortho isomer is rare; and usually a mixture of DVBDO is mostly produced as an about 2:1 ratio of meta (Structure V) to para (Structure VI). Thus, the present invention preferably includes as one embodiment a 2:1 ratio of Structure V to Structure VI.

The viscosity of the divinylarene dioxides produced by the process of the present invention ranges generally from about 0.01 Pa·s to about 0.1 Pa·s; preferably, from about 0.01 Pa·s to about 0.05 Pa·s; and more preferably, from about 0.01 Pa·s to about 0.025 Pa·s at 25° C. In one embodiment, the process of the present invention is particularly suited for the preparation of DVBDO, a liquid epoxy resin having a liquid viscosity of less than about 0.02 Pa·s.

The utility of the divinylarene dioxides of the present invention requires thermal stability to allow formulating or processing the divinylarene dioxides at moderate temperatures (for example, at temperatures of from about 100° C. to about 200° C.) for up to several hours (for example, for at least 2 hours) without oligomerization or homopolymerization. Oligomerization or homopolymerization during formulation or processing is evident by a substantial increase (e.g., greater than 50 fold) in viscosity or gelling (crosslinking). The divinylarene dioxides of the present invention have sufficient thermal stability such that the divinylarene dioxides do not experience a substantial increase in viscosity or gelling during formulation or processing at the aforementioned moderate temperatures.

The divinylarene dioxide products of the present invention are useful for the preparation of epoxy resin compositions or formulations which, in turn, are useful for preparing thermosets or cured products in the form of coatings, films, adhesives, laminates, composites, electronics, and the like.

The divinylarene dioxide products of the present invention are useful for the preparation of epoxy resin compositions or formulations which, in turn, are useful for preparing thermosets or cured products in the form of coatings, films, adhesives, laminates, composites, electronics, and the like.

As an illustration of the present invention, in general, resin compositions based on the divinylarene dioxide products of the present invention may be useful for casting, potting, encapsulation, molding, and tooling. The present invention is particularly suitable for all types of electrical casting, potting, and encapsulation applications; for molding and plastic tooling; and for the fabrication of vinyl ester resin based composites parts, particularly for producing large vinyl ester resin-based parts produced by casting, potting and encapsulation. The resulting composite material may be useful in some applications, such as electrical casting applications or electronic encapsulations, castings, moldings, potting, encapsulations, injection, resin transfer moldings, composites, coatings and the like.

EXAMPLES

The following examples and comparative examples further illustrate the present invention in detail but are not to be construed to limit the scope thereof. The product mixtures prepared in the Examples which follow were analyzed by standard gas chromatography (GC) analytical equipment and methods.

Various terms and designations used in the following examples are explained herein as follows: "DVB" stands for divinylbenzene; "DVBDO" stands for divinylbenzene dioxide; "DVBMO" stands for divinylbenzene monoxide; and "EVB" stands for ethylvinylbenzene.

For each of the following preparations in the Examples, 80% DVB was used containing 20% EVB but the yields and final compositions are referred to DVB. All chemicals were purchased from Sigma-Aldrich and used without further purifications. Perbenzoic acid was synthesized using literature procedures such as for example as described in Organic Synthesis Coll., Vol. 5, p. 904, 1973. Monoperphthalic acid was synthesized using literature procedures such as for example as described in Organic Synthesis Coll., Vol. 3, p. 619, 1955.

Example 1

DVB (2 mmol) and dichloromethane (5 mL) were transferred into a three necked flask equipped with stirring and temperature controllers, condenser, and addition port. An aqueous solution of potassium carbonate (6 mmol in 15 mL water) was added to the flask to form a stirred reaction mixture. M-chloroperbenzoic acid (6 mmol) was dissolved in dichloromethane (15 mL) and then the resulting solution was added to the stirred reaction mixture in the course of 30 minutes. The reaction temperature was kept at 25° C. and the pH of the reaction mixture was maintained at 7-8. After two hours, the resulting organic phase was analyzed by GC. No DVB or DVBMO was detected and 75% DVBDO was formed.

Example 2

DVB (2 mmol) and dichloromethane (5 mL) were transferred into a three necked flask equipped with stirring and temperature controllers, condenser, and addition port. An aqueous solution of sodium-hydrogen carbonate (6 mmol in 15 mL water) was added to the flask to form a stirred reaction mixture. Solid m-chloroperbenzoic acid (6 mmol) was added to the stirred reaction mixture in the course of 30 minutes. The reaction temperature was kept at 25° C. and the pH of the reaction mixture was maintained at 7-8. After two hours, the resulting organic phase was analyzed by GC. No DVB or DVBMO was detected and 97% DVBDO was formed.

Example 3

DVB (2 mmol) and dichloromethane (5 mL) were transferred into a three necked flask equipped with stirring and temperature controllers, condenser, and addition port.

M-chloroperbenzoic acid (6 mmol) was added to the stirred reaction mixture in the course of 30 minutes. The reaction temperature was kept at 25° C. The reaction was complete after 6 hours and the reaction mixture was analyzed by GC. No DVB was detected. Also, 0.5% DVBMO and 91% DVBDO were detected.

Example 4

DVB (3 mmol), pyrazole (3 mmol) and dichloromethane (5 mL) were transferred into a three necked flask equipped with stirring and temperature controllers, condenser, and addition port. M-chloroperbenzoic acid (9 mmol) in dichloromethane solution (30 mL) was added to the stirred reaction mixture in the course of 30 minutes. The reaction temperature was kept at 25° C. The reaction was complete after 1 hour, the reaction mixture was analyzed by GC. No DVB, no DVBMO was detected and 95% DVBDO was formed.

Example 5

DVB (6 mmol) was transferred into a three necked flask equipped with stirring and temperature controllers, condenser, and addition port. Perbenzoic acid (18 mmol) in dichloromethane solution (10 mL) was added to the stirred reaction mixture in the course of 30 minutes. The reaction temperature was kept at 25° C. Reaction was complete after 3 hours, the reaction mixture was analyzed by GC. No DVB, no DVBMO was detected and 98% DVBDO was formed.

Example 6

DVB (6 mmol) and $NaHCO_3$ buffer (0.9M, 30 mL) were transferred into a three necked flask equipped with stirring and temperature controllers, condenser, and addition port. Perbenzoic acid (18 mmol) in dichloromethane solution (16 mL) were added to the stirred reaction mixture in the course of 30 minutes. The reaction temperature was kept at 25° C. and the pH of the reaction mixture was maintained at 7-8. After two hours, the phases were separated and the organic phase was washed with $Na_2SO_3$ (0.5M, 15 mL) three times, then three times with $NaHCO_3$ (0.9M, 15 mL), finally once with water (15 mL). The dichloromethane solution was dried over $Na_2SO_4$ and evaporated to dryness, resulting in 80% isolated DVBDO yield. The resulting oil was analyzed by GC. No DVB or DVBMO were detected in the resulting oil. However, the oily product produced was 97% DVBDO.

Example 7

DVB (6 mmol) and an aqueous solution of sodium-hydrogen carbonate (0.9M, 20 mL) were transferred into a three necked flask equipped with stirring and temperature controllers, condenser and addition port. Solid perbenzoic acid (18 mmol) was added to the stirred reaction mixture in the course of 30 minutes. The reaction temperature was kept at 25° C. and the pH of the reaction mixture was maintained at 7-8. After two hours, the resulting organic phase was analyzed by GC. No DVB or DVBMO was detected and 96% DVBDO was formed.

Example 8

DVB (1 mmol) and MeOH (10 mL) were transferred into a 20 mL vessel equipped with a reflux condenser along with monoperphthalic (4 mmol). The mixture was heated to 50° C. for 6 hours. Analysis by GC showed 55% conversion of DVB and a 38% yield of DVBDO.

What is claimed is:

1. A process for preparing a divinylarene dioxide comprising reacting (a) at least one divinylarene; (b) at least one basic compound; (c) at least one oxidant; wherein the oxidant comprises a peracid oxidant capable of reacting with the divinylarene tinder reaction conditions to form a divinylarene dioxide product at a yield of greater than 50 percent.

2. The process of claim 1, wherein the divinylarene, the basic compound, and the peracid oxidant reaction is carried out under homogeneous reaction conditions.

3. The process of claim 1, wherein the oxidant comprises an aliphatic peracid oxidant or an aromatic peracid oxidant.

4. The process of claim 1, wherein the reaction of the divinylarene, the basic compound, and the peracid oxidant is carried out under heterogeneous conditions sufficient to form a divinylarene dioxide product.

5. The process of claim 1, wherein the peracid oxidant comprises performic acid, peracetic acid, m-chloroperbenzoic acid, perbenzoic acid, monoperphthalic acid, and mixtures thereof.

6. The process of claim 1, wherein the peracid oxidant is added to the reaction mixture as a solid; or wherein the peracid compound is first mixed in a solution and then the solution subsequently added the reaction mixture.

7. A process for preparing a divinylarene dioxide comprising reacting (a) at least one divinylarene; (b) at one basic compound; (c) at least one oxidant; wherein the oxidant comprises a peracid compound capable of reacting with the divinylarene under reaction conditions to form a divinylarene dioxide product at a yield of greater than 50 percent, and wherein the peracid oxidant used in the reaction is generated in-situ.

8. The process of claim 1, including a solvent; and wherein the solvent comprises chlorinated hydrocarbons; aromatic hydrocarbons; polar solvents; ethers; alcohols; fluorinated alcohols; or mixtures thereof.

9. The process of claim 1, wherein the at least one divinylarene is divinylbenzene; and wherein the divinylarene dioxide formed is divinylbenzene dioxide.

10. The process of claim 1, wherein the reaction is carried out at a temperature within the range of from about 0° C. to about 100° C.

11. The process of claim 1, wherein the concentration of the at least one divinylarene ranges from about 1 weight percent to about 100 weight percent; and wherein the molar ratio of the oxidant compared to the divinylarene in the present invention ranges from about 1 mol/mol to about 20 mol/mol.

12. The process of claim 1, further including the step of separating the divinylarene dioxide reaction product from residual components of the reaction mixture by a separation method; and wherein the separation method comprises chromatography, precipitation, extraction, filtration, or distillation.

13. The process of claim 1, further including the step of purifying the divinylarene dioxide reaction product; and wherein the divinylarene dioxide reaction product is purified by distillation.

14. The process of claim 1, wherein the basic compound is sodium carbonate, potassium carbonate, sodium-hydrogencarbonate, potassium-hydrogencarbonate, sodium phosphate, potassium phosphate or mixtures thereof.

15. The process of claim 1, wherein the basic compound is added to the reaction mixture as a solid; or wherein the basic compound is added to the reaction mixture as an aqueous solution.

16. The process of claim 1, wherein the molar ratio of the basic compound compared to the peracid compound ranges about 0.5 mol/mol to about 5 mol/mol.

17. The process of claim 15, wherein the pH of aqueous phase is from about 5 to about 11.

18. A process for preparing a divinylarene dioxide comprising reacting (a) at least one divinylarene; (b) at one basic compound; (c) at least one oxidant; wherein the oxidant comprises a peracid compound capable of reacting with the divinylarene under reaction conditions to form a divinylarene dioxide product at a yield of greater than 50 percent; and (d) a phase transfer agent; wherein the phase transfer agent comprises tetraakyl, tetraaryl, or mixed alkyl-aryl ammonium hydroxides or salts; and mixtures thereof.

19. The process of claim 18, wherein the phase transfer agent includes tetrabutylammonium hydroxide, tetrabutylammonium chloride, tetrabutylammonium acetate; tetraphenylammonium hydroxide, chloride tetraphylammonium acetate or mixtures thereof.

20. The process of claim 18, wherein the molar ratio of the divinylarene and phase transfer agent ranges from about 0.01 mol/mol to about 5 mol/mol.

21. The process of claim 1, wherein the basic compound is a miscible organic base; and wherein the organic base is an aliphatic amine, a heteroaromatic compound or mixtures thereof.

22. The process of 21, wherein the organic base is pyrazole, imidazole, pyridine, triethyl amine, or mixtures thereof.

\* \* \* \* \*